United States Patent
Kocal et al.

[11] Patent Number: 5,962,760
[45] Date of Patent: *Oct. 5, 1999

[54] ALKYLATION OF AROMATICS USING A METAL CATION-MODIFIED FRIEDEL-CRAFTS TYPE CATALYST

[75] Inventors: Joseph A. Kocal, Gurnee; Anil R. Oroskar, Downers Grove, both of Ill.

[73] Assignee: UOP LLC, Des Plaines, Ill.

[ * ] Notice: This patent is subject to a terminal disclaimer.

[21] Appl. No.: 08/905,762

[22] Filed: Aug. 4, 1997

Related U.S. Application Data

[63] Continuation-in-part of application No. 08/533,576, Sep. 25, 1995, Pat. No. 5,672,797, which is a continuation-in-part of application No. 08/265,161, Jun. 24, 1994, abandoned, and a continuation-in-part of application No. 08/093,150, Jul. 19, 1993, abandoned.

[51] Int. Cl.⁶ .............................. C07C 2/68; C07C 2/66; C07C 2/64
[52] U.S. Cl. .................... 585/468; 585/467; 585/459; 585/463; 585/460; 585/448
[58] Field of Search ................... 585/467, 459, 585/463, 460, 448, 468

[56] References Cited

U.S. PATENT DOCUMENTS

| | | | |
|---|---|---|---|
| 2,999,074 | 9/1961 | Bioch et al. | 252/442 |
| 3,318,820 | 5/1967 | Muller et al. | 252/415 |
| 4,048,248 | 9/1977 | Ryu | 260/671 P |
| 4,358,362 | 11/1982 | Smith et al. | 208/91 |
| 4,463,207 | 7/1984 | Johnson | 585/462 |
| 5,672,797 | 9/1997 | Kocal | 585/467 |

*Primary Examiner*—Hien Tran
*Assistant Examiner*—Thuan D. Dang
*Attorney, Agent, or Firm*—Thomas K. McBride; Frank S. Molinaro; Maryann Maas

[57] ABSTRACT

A process for the alkylation of aromatic compounds with an olefin or alkyl halide having from 1 to 24 carbon atoms utilizes a novel catalyst comprising: a) a refractory inorganic oxide, b) the reaction product of a first metal halide and bound surface hydroxyl groups of the refractory inorganic oxide, c) a second metal cation, and d) optionally a zerovalent third metal. The refractory inorganic oxide is selected from the group consisting of alumina, titania, zirconia, chromia, silica, boria, silica-alumina, and combinations thereof and the first metal halide is a fluoride, chloride, or bromide of aluminum, gallium, zirconium, or boron. The second metal cation is selected from the group consisting of: monovalent metal cations in an amount from 0.0026 up to about 0.20 gram atoms per 100 grams refractory inorganic oxide for lithium, potassium, cerium, rubidium, silver, and copper, and from 0.012 to about 0.20 gram atoms for sodium; and alkaline earth metal cations in an amount from about 0.0013 up to about 0.01 gram atoms per 100 grams of refractory inorganic oxide for beryllium, strontium, and barium, and in an amount from about 0.004 up to about 0.1 gram atoms per 100 grams support for magnesium and calcium, or combinations thereof. The third metal is selected from the group consisting of platinum, palladium, nickel ruthenium, rhodium, osmium and iridium, and any combination thereof. These novel catalysts are effective in other alkylation reactions including motor fuel alkylation.

13 Claims, No Drawings

ALKYLATION OF AROMATICS USING A METAL CATION-MODIFIED FRIEDEL-CRAFTS TYPE CATALYST

CROSS REFERENCE TO RELATED APPLICATION

This application is a continuation-in-part of my application Ser. No. 08/533,576 now U.S. Pat. No. 5,672,797, filed Sep. 25, 1995, which is a continuation-in-part of Ser. No. 08/265,161, filed Jun. 24, 1994, now abandoned, which is a continuation-in-part of Ser. No. 08/093,150, filed Jul. 19, 1993, now abandoned, all of which are hereby incorporated by reference.

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates as initially prepared had substantial branching in the alkyl chain. This situation was maintained until the early 1960's when it became apparent that the branched alkyl-based detergents were contributing to the pollution of lakes and streams and forming relatively stable foams. Examination of the problem showed that the branched structure of the alkyl chains was not susceptible to rapid biodegradation and the surfactant properties of the detergent thus persisted for long periods of time. This was not the case earlier when natural soaps were used because of the rapid biodegradation of the linear chains in natural soaps.

After recognizing the biodegradability of ABS based on alkylation by linear olefins, industry turned its attention to the production of these unbranched olefins and their subsequent use in the production of linear alkyl benzenes. Processes were developed for efficient alkylation of benzene by available feedstocks containing linear olefins, and the production of linear alkyl benzenes (LAB) became another reliable process broadly available to the petroleum and petrochemical industry. It gradually evolved that HF-catalyzed alkylation was particularly effective in LAB production, and an HF-based alkylation process became the industry standard.

With increasing environmental concern came increasing disenchantment with HF as a catalyst and a concomitant need to find a substitute equal or superior to it in all respects. As regards criteria in addition to the price, the extent of conversion effected by the catalyst, the selectivity of monoalkylbenzene formation, and the linearity of alkylbenzenes produced loomed large. At this point the definition of several terms are necessary to adequately understand and appreciate what follows.

Alkylation typically is performed using an excess of benzene relative to olefins. The ideal catalyst would show 100% conversion of olefins using an equal molar proportion of benzene and olefins, but since this has not been attainable one strives for maximum olefin conversion using a benzene to olefin molar ratio up to about 30. The better the catalyst, the lower will be the benzene:olefin ratio at a high conversion of, say, 98%. The degree of conversion at a constant value of benzene-olefin ratio is a measure of catalytic activity (subject to the caveat that the ratio must not be so high that the degree of conversion is invariant to small changes in this ratio). The degree of conversion may be expressed by the formula, $$V = \frac{C}{T} \times 100,$$

where V equals percent conversion, C equals moles of olefin consumed, and T equals moles olefin initially present.

However active the catalyst may be, it is not valuable unless it also is selective. Selectivity is defined as the percentage of total olefin consumed under reaction conditions which appears as monoalkylbenzene and can be expressed by the equation, $$S = \frac{M}{C} \times 100,$$

where S equals selectivity, M equals moles of monoalkylbenzenes produced, and C equals moles olefin consumed. The better the selectivity, the more desirable is the catalyst. An approximate measure of selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S>85%) the results calculated from the two equations are nearly identical. The latter of the foregoing two equations is routinely used in commercial practice because of the difficulty in distinguishing between oligomers and polyalkylbenzenes.

Finally, the reaction of linear olefins with benzene in principal proceeds according to the equation, $$C_6H_6 + R_1CH=CHR_2 \rightarrow C_6H_5CH(R_1)CH_2R_2 + C_6H_5CH(R_2)CH_2R_1.$$

Note that the side chain is branched solely at the benzylic carbon and contains only one branch in the chain. Although strictly speaking this is not a linear alkylbenzene, nonetheless the terminology which has grown up around the process and product in fact includes as linear alkylbenzenes those materials whose alkyl group chemically arises directly from linear olefins and therefore includes alpha-branched olefins. Because alkylation catalysts also may induce the rearrangement of olefins to give products which are not readily biodegradable (vide supra), for example, α,α-disubstituted olefins which subsequently react with benzene to afford an alkyl benzene with branching at other than the benzylic carbon,

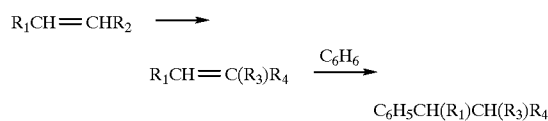

the degree to which the catalyst effects formation of linear alkyl benzenes is another important catalyst parameter. The degree of linearity can be expressed by the equation, $$D = \frac{L}{M} \times 100,$$

where D equals degree of linearity, L equals moles of linear monoalkyl benzene produced, and M equals moles of monoalkyl benzene produced.

Consequently, the ideal catalyst is one where V equals 100, S equals 100, and D equals 100. The minimum requirement is that linearity be at least 90% at a selectivity of at least 85% and at a conversion of at least 98%. These are minimum requirements; that is, if a catalyst fails to meet all of the foregoing requirements simultaneously the catalyst is commercially unacceptable.

The linearity requirement is assuming added importance and significance in view of the expectation in some areas of minimum standards for linearity in detergents of 92–95% near-term, increasing to 95–98% by about the year 2000. Since the olefinic feedstock used for alkylation generally contains a small percentage of non-linear olefins—a non-liner olefin content of about 2% is common to many processes—the requisite linearity in the detergent alkylate places even more stringent requirements on catalytic performance; the inherent linearity of the alkylation process must increase by the amount of non-linear olefins present in the feedstock. For example, with a feedstock containing 2% non-linear olefins the catalyst must effect alkylation with 92% linearity in order to afford a product with 90% linearity, and with a feedstock containing 4% non-linear olefins the catalyst must effect alkylation with 94% linearity to achieve the same result.

Our solution to the problem of identifying a catalyst for detergent alkylation which satisfies all the aforementioned criteria, and which in particular meets the increasingly stringent requirements of linearity, arose from our observation that the isomerization of linear olefins to non-linear olefins—this is the process ultimately responsible for non-linear detergent alkylate arising from a linear olefin feedstock—is quite sensitive to temperature but relatively insensitive to the particular candidate catalyst for the detergent alkylate process. This result was itself quite surprising, but more importantly it suggested that effecting alkylation at a lower temperature was the key to greater product linearity. Our focus then shifted to finding more active catalysts, i.e., materials which would catalyze detergent alkylation at lower temperatures.

The importance of our observation that temperature is the major factor in olefin isomerization and that the particular catalyst plays only a minor role cannot be overemphasized, for it permits one to focus solely on methods of reducing the alkylation temperature. Since the other requisites of a detergent alkylation process can be addressed in other ways, our observation significantly foreshortens the focus on ways to obtain an improved process. A result of our observation is the novel use of a solid acid catalyst to craft a new process permitting alkylation at a substantially lower temperature than that previously attainable using other members of this class of catalysts.

SUMMARY OF THE INVENTION

The object of this invention is to prepare linear alkylbenzenes by the alkylation of benzene with an olefin, particularly in a continuous manner, where alkylation proceeds with at least 90% selectivity of olefin conversion to monoalkylbenzenes, and with at least 90% linearity with respect to monoalkylbenzene formation. In an embodiment benzene in a total of from 5 to about 30 molar proportions is reacted with 1 molar proportion of a linear monoolefin, or a mixture of linear monoolefins, in the presence of a catalyst which is a composite of a Friedel-Crafts type metal halide bound to the surface hydroxyl groups of refractory inorganic oxide, a zerovalent metal having hydrogenation activity, and another metal cation. In a more specific embodiment the linear monoolefins have from 6 up to about 20 carbon atoms. In a still more specific embodiment the molar proportion of total benzene relative to total linear monoolefins is from about 8:1 to about 20:1. Other embodiments will be apparent from the ensuing description.

A broader object of this invention is a process for the liquid phase alkylation of aromatic compounds with a variety of alkylating agents using as a catalyst the aforementioned composite. In a specific embodiment of this branch of our invention the alkylating agent is an olefin containing up to about 24 carbon atoms. In another embodiment the alkylating agent is an alcohol containing from 1 up to about 24 carbon atoms.

DESCRIPTION OF THE INVENTION

In our search for catalysts in a detergent alkylation process, and especially solid catalysts capable of being used as a bed in a continuous fixed bed detergent alkylation process, it soon became clear that the degree of branching in the alkyl chain of the resulting alkylbenzene (detergent alkylate) was principally a function of temperature, with lower reaction temperatures affording lower branching. Since linearity of the alkyl chain is an increasingly important environmental and regulatory consideration, our observation led to a search for catalysts which would effect alkylation in a continuous process at acceptable productivity rates and at a temperature not exceeding 140° C. For the purpose of this application an acceptable productivity means an olefin liquid hourly space velocity of at least 0.05 $hr^{-1}$. What we have found is that certain modified Friedel-Crafts type catalysts, where the metal halide is reacted with the surface hydroxyl groups of refractory organic oxides, having coimpregnated zerovalent metals with hydrogenation activity and monovalent or divalent metal cations, principally of the alkali metal or alkaline earth metal series, are quite suitable catalysts for a detergent alkylation process at temperatures not exceeding 140° C. and effect detergent alkylation with at least 90% selectivity to monoalkylbenzenes and with at least 90% linearity of the alkyl side chain. Although our invention is particularly relevant to detergent alkylation, it is important to understand that our invention is generally applicable to the alkylation of alkylatable aromatic compounds with a large universe of alkylating agents, as will be clear from the material within.

The feedstocks containing the alkylating agent which are used in the practice of that branch of our invention applicable to detergent alkylation normally result from the dehydrogenation of paraffins. Since the entire dehydrogenation reaction mixture often is used, the reaction is not run to completion to minimize cracking, isomerization, and other undesirable and deleterious byproducts. The branched olefins which are formed are not removed, yet the total amount of nonlinear alkylbenzene formed still must be sufficiently small that the monoalkylate meets the requirements of 90% linearity. The polyolefins formed during dehydrogenation are minimized in the feedstocks used in the practice of this invention. Consequently the feedstocks are largely a mixture of unreacted paraffins and unbranched, linear monoolefins which typically are in the C6–C20 range, although those in the C8–C16 range are preferred in the practice of this invention, and those in the C10–C14 range are even more preferred. Unsaturation may appear anywhere on the linear monoolefin chain; there is no requirement as to the position of the double bond, but only a requirement as to the linearity of the olefin. See R. A. Myers, "Petroleum Refining Processes", 4-36 to 4-38. (McGraw-Hill Book Company), 1986.

In the broader case the alkylating agent is an olefin, an alcohol, or an alkyl halide containing from 1 up to about 24 carbon atoms. Where the alkylating agent is an olefin the latter may be either branched or unbranched and also may be substituted with, for example, an aromatic substituent. Examples of suitable olefins include ethylene, propylene, the butenes, pentenes, hexenes, heptenes, octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, and tetracosenes. Further examples include styrene, phenylpropene, phenylbutene, phenylpentene, phenylhexene, and so forth.

Another class of alkylating agents which may be used in the practice of our invention are alcohols. Like the olefins, the alkyl chain in the alcohol may be branched or unbranched and the hydroxyl group may be found anywhere on the alkyl chain. That is, there is no particular requirement as to the spatial position of the hydroxyl moiety on the alkene chain. Examples of alcohols which may be successfully used in our invention include methanol, ethanol, propanol, butanol, pentanol, hexanol, heptanol, octanol, nonanol, decanol, undecanol, tetradecanol, and so forth. Especially relevant to this branch of the invention is methanol as the alcohol.

The last of the three classes of alkylating agents which may be frequently used in the practice of this invention are alkyl halides. Alkyl chlorides are probably the most widely used alkyl halides, but alkyl bromides also may be successfully used in the practice of our invention. As with alcohols, the paraffinic chain may be either branched or unbranched and the halogen may be found at any position along the chain. Suitable examples of alkyl halides include propyl chloride, propyl bromide, butyl chloride, butyl bromide, pentyl chloride, pentyl bromide, hexyl chloride, hexyl bromide, heptyl chloride, heptyl bromide, benzyl chloride, benzyl bromide, xylyl chloride, xylyl bromide, phenethyl chloride, phenethyl bromide, allyl chloride, allyl bromide, butenyl chloride, butenyl bromide, and so forth.

Where the process is detergent alkylation, the linear monoolefins in the feedstock are reacted with benzene. Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist of not only the desired monoalkylbenzenes, but would also contain large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect on both conversion and, perhaps more importantly, selectivity of the alkylation reaction. In order to carry out alkylation with the conversion, selectivity, and linearity required using the catalysts of our process, a total benzene::linear monoolefin molar ratio of from 5:1 up to as high as 30:1 is recommended, although the process normally operates satisfactorily at a total benzene:linear monoolefins molar ratio between about 8:1 and about 20:1.

In the more general case the alkylating agent is reacted with an alkylatable aromatic compound. Such aromatic compounds are selected from the group consisting of benzene, naphthalene, anthracene, phenanthracene, and substituted derivatives thereof. The most important class of substituents are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds include benzene, naphthalene, anthracene, phenanthrene, biphenyl, toluene, xylene, ethylbenzene, phenol, anisole, propylbenzene, butylbenzene, pentylbenzene, hexylbenzene, heptylbenzene, octylbenzene, and so forth; anisole, ethoxy-, propoxy-, butoxy-, pentoxy-, hexoxybenzene, and so forth.

Where the process is detergent alkylation, the benzene and linear monoolefins in the $C_6$–$C_{20}$ range, are reacted in the presence of a catalyst under alkylation conditions. These alkylation conditions include a temperature in the range between about 60° C. and 140° C., and preferably in the range from 70 to 135° C. Since the alkylation is conducted as a liquid phase process, pressures must be sufficient to maintain the reactants in the liquid state. The requisite pressure necessarily depends upon the feedstock and temperature, but normally is in the range of 200–1000 psig (1379–6985 kPa), and most usually 300–500 psig (2069–3448 kPa).

In the more general case, there is a wide variation in the alkylation conditions of an alkylatable aromatic compound by an alkylating agent depending upon the reactivity of the two reactants. For example, for hydroxy benzenes (phenols) the hydroxyl moiety is found to be a quite activating group toward alkylation, and therefore the hydroxy benzenes are readily alkylated so that temperatures of no more than about 150° C. suffice. On the other hand, where the aromatic is an unsubstituted aromatic, such as benzene, and the alkylating agent is a lower olefin, such as propylene, temperatures as high as 400° C. may be necessary. Consequently, the temperature range appropriate for alkylation will be between about 60 and about 400° C., with the most usual temperature range being between 100 and 225° C. As regards pressures, since the alkylation is desirably conducted as a liquid phase process the reaction pressure must be sufficient to maintain the reactants in the liquid stage. This is the sole pressure requirement for the practice of this invention, and since a wide variety of alkylatable aromatics compounds and alkylating agents may be used in the practice of this invention it can be readily appreciated that there exists a wide variation in reaction pressure, from atmospheric up to as high as about 2000 pounds per square inch (14,000 kPa).

The alkylation of benzene by linear monoolefins with the requisite conversion, selectivity, and linearity is effected by the catalysts of our invention which can be referred to as metal cation-modified Friedel-Crafts type metal halides supported on refractory inorganic oxides via reaction of their surface hydroxyl groups with the metal halide, where the refractory inorganic oxide also is optionally coimpregnated with at least one metal having hydrogenation activity. The analogs of our catalyst without the metal cations of our invention are well known in the art (see U.S. Pat. Nos. 2,999,074; cf. 3,318,820) and the extensive descriptions of their preparations are applicable to our catalyst with the exception of impregnation with a monovalent cation or alkaline earth metal cation. Thus, much of the prior art description is applicable to our catalysts and makes a detailed description of their preparation unnecessary. The following description then will suffice merely to afford the reader an understanding of our invention.

The refractory inorganic oxides suitable for use in this invention have a surface area of at least about 35 $m^2/g$, preferably greater than about 50 $m^2/g$, and more desirably greater than 100 $m^2/g$. There appears to be some advantage to working with materials having as high a surface area as possible, although exceptions are known which preclude making this a general statement. Suitable refractory inorganic oxides include alumina, titania, zirconia, chromia, silica, boria, silica-alumina, and combinations thereof. Of these alumina is particularly preferred. Any alumina phase may be used so long as it has a surface area of at least 35 $m^2/g$ and has surface hydroxyl groups, which for all practical matters excludes alpha-alumina. Among the phases which may be used are included gamma-, etc-, and theta-alumina, although the various phases are not necessarily equivalent in their effectiveness as an alkylation catalyst. Aluminum phosphate is another favored refractory material.

It is required that the refractory inorganic oxide have bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of adsorbed water is generally detrimental to the preparation of the catalysts of our invention, the refractory inorganic oxides are first treated to remove surface hydroxyl groups arising from water, most usually by calcination at a temperature which specifically and preferentially removes physically adsorbed water without chemically altering the other hydroxyl groups. For example, calcination temperatures ranging from about 350° C. to about 700° C. are usually satisfactory where the inorganic oxide is alumina.

The catalytic composites of our invention optionally contain a metal having hydrogenation activity. Although the presence of this component is not necessary for alkylation activity, we have found its presence may be desirable in subsequent catalyst regeneration. Where a hydrogenation-active metal is present it generally is deposited on the refractory inorganic oxide prior to the reaction of its bound surface hydroxyl groups with metal halides. Although such a procedure has proven both convenient and effective, we do not wish to imply that this is the only sequence which may be used to afford an effective catalyst. Metals which have been found to be particularly effective include nickel and the noble metals of platinum, palladium, ruthenium, rhodium, osmium, and iridium, although platinum and palladium are by far the most desirable of the noble metals. The desired metal may be composited with the refractory inorganic oxide in any desired manner, such as by impregnation, coprecipitation, dipping, and so forth, of a suitable salt followed by reduction of the metal to its zerovalent state. Such methods are well known and need not be described here. Hydrogenation-active metal levels may range between about 0.01 up to about 1.0 weight percent for the noble metals, based on the weight of the finished catalyst, and from about 0.1 up to about 5 weight percent for nickel. The composite of the metal and refractory inorganic oxide is dried and calcined under controlled conditions to remove physically adsorbed water but under sufficiently mild conditions so that the "chemically combined" hydroxyl groups are not eliminated.

The more usual way of introducing a hydrogenation-active metal into the catalytic composites of our invention is by coimpregnation of the refractory inorganic oxide with a salt of the hydrogenation-active metal together with one or more monovalent or alkaline earth metal cations of our invention. But as stated above it is not believed that the particular procedure or sequence used is determinative of success of, or even of substantial significance to, the final catalytic composite.

The next stage in the preparation of our catalytic composites, whether or not a metal with hydrogenation activity has been deposited thereon, is to deposit on the composite one or more monovalent metal or alkaline earth metal cations. Such metals include lithium, sodium, potassium, cesium, rubidium, silver, copper(I), beryllium, magnesium, calcium, strontium, and barium. Among the monovalent metal cations the alkali metal cations are favored. The amount of metal cation which is impregnated on the composite is in most cases an amount having a gram atom equivalent from about 0.1 up to about 8 weight percent potassium, which is 0.0026 gram atoms potassium up to 0.2 gram atoms per 100 gram support. We define a "gram atom equivalent" of another metal cation as being a number of gram atoms of the metal divided by its valence per 100 grams support. For example, for most divalent atoms the gram atom equivalent is 0.0013 up to about 0.1 gram atoms per 100 gram support.

There is some irregularity in the amount of metal cations which are to be impregnated upon the refractory inorganic oxides which are the supports in our invention. For the monovalent cations of lithium, potassium, cesium, rubidium, silver and copper, the amounts deposited are from 0.0026 to about 0.20 gram atom per 100 grams support; for sodium the amount is from 0.009 to about 0.20 gram atom per 100 grams support. For the divalent cations beryllium, strontium, and barium the amount is from 0.0013 to about 0.1 gram atoms per 100 gram support; for magnesium and calcium the amount is from 0.004 to about 0.1 gram atoms per 100 gram support. These amounts in terms of grams of metal cation per 100 gram support are summarized in the following table. Since the preferred range is from 0.012 up to about 0.12 gram atoms for monovalent cations, and 0.006 up to about 0.06 gram atoms for divalent metal cations, the preferred ranges also are listed in the following table. It needs to be emphasized that in all cases the minimum amount of cation added is well outside that normally found as impurities in the supports of our invention, hence will not be present incidental to their preparation.

TABLE

| | Amounts of Metal Cations on Supports (grams per 100 gram support) | | | |
|---|---|---|---|---|
| | Range | | Preferred Range | |
| Metal Cation | Minimum | Maximum | Minimum | Maximum |
| Monovalent | | | | |
| Lithium | 0.02 | 1.4 | 0.1 | 0.8 |
| Sodium | 0.2 | 4.6 | 0.3 | 2.8 |
| Potassium | 0.1 | 7.8 | 0.5 | 4.7 |
| Cesium | 0.3 | 26.6 | 1.6 | 15.9 |

TABLE-continued

Amounts of Metal Cations on Supports
(grams per 100 gram support)

| Metal Cation | Range | | Preferred Range | |
| --- | --- | --- | --- | --- |
| | Minimum | Maximum | Minimum | Maximum |
| Rubidium | 0.2 | 17.1 | 1.0 | 10.3 |
| Copper(I) | 0.2 | 12.7 | 0.8 | 7.6 |
| Silver | 0.3 | 21.6 | 1.3 | 12.9 |
| Divalent | | | | |
| Beryllium | 0.01 | 0.9 | 0.1 | 0.5 |
| Magnesium | 0.1 | 2.4 | 0.1 | 1.5 |
| Calcium | 0.2 | 4.0 | 0.2 | 2.4 |
| Strontium | 0.1 | 8.8 | 0.5 | 5.3 |
| Barium | 0.2 | 13.7 | 0.8 | 8.2 |

Impregnation of the composite by the monovalent metal or alkaline earth metal cation may be done simply by mixing the composite with a suitable aqueous solution of the salt and removing water. The particular monovalent or alkaline earth metal salt used is not especially important so long as it provides sufficient solubility in water. As a practical matter, the halides, nitrates, and acetates may be the most commonly employed salts. Salts prone to precipitation should be avoided in order to avoid non-uniform impregnation, but otherwise there are no serious limitations on the salts which may be used. After evaporation of excess water, materials generally are dried at a temperature between about 100 and 200° C. for 24 hours and then calcined at a temperature which specifically and preferentially removes physically adsorbed water without chemically altering the other hydroxyl groups. As mentioned before, temperatures ranging from about 350° C. to about 700° C. usually are satisfactory where the inorganic oxide is alumina.

Subsequent to metal deposition and calcination, the bound surface hydroxyl groups of the refractory inorganic oxide are reacted with a metal halide having Friedel-Crafts activity. Among the metals which may be used are included aluminum, zirconium, tin, tantalum, titanium, gallium, antimony, and boron. Suitable halides are the fluorides, chlorides, and bromides. Representative of such metal halides include aluminum chloride, aluminum bromide, ferric chloride, ferric bromide, zirconium chloride, zirconium bromide, boron trifluoride, titanium tetrachloride, gallium chloride, tin tetrachloride, antimony fluoride, tantalum chloride, tantalum fluoride, and so forth. Of these metal halides the aluminum halides are preferred, especially aluminum chloride. Except for boron trifluoride, the chlorides are generally the preferable halides.

The reaction between the metal halides of this invention and the bound surface hydroxyl groups of the refractory inorganic oxide is readily accomplished by, for example, sublimation or distillation of the metal halide onto the surface of the particles of the metal inorganic oxide composite. The reaction is attended by the elimination of between about 0.5 and 2.0 moles of hydrogen halide per mole of metal halide adsorbed thereon. The reaction temperature will depend upon such variables as the reactivity of the metal halides and its sublimation temperature or boiling point, where the metal halide is reacted in the gas phase, as well as on the nature of the refractory inorganic oxide. For example, using aluminum chloride and alumina as our specific examples reaction readily occurs within the range between about 190 through 600° C.

The amount of metal halide which is reacted with the bound surface hydroxyl groups of the refractory inorganic oxide is generally given in terms of the weight percent of the Friedel-Crafts metal on the composite. This amount will vary with the refractory inorganic oxide used, the relative number of bound surface hydroxyls of the inorganic oxide (which may be related to the particular oxide phase utilized), the specific Friedel-Crafts metal halide employed, as well as the particular procedure used to effect reaction between the Friedel-Crafts type metal halide and the bound surface hydroxyl. As a rough rule of thumb for aluminum chloride on alumina, as an example, the amount of aluminum chloride reacted expressed as weight percent aluminum in the final composite ranges from about 0.1 up to about 2.5%, with the level being a function primarily of the number of bound surface hydroxyl groups on the refractory inorganic oxide.

It has been found that the catalysts of my invention are quite sensitive to water. Thus it is desirable that the feedstocks be dried to a level of 1 ppm or less, most preferably to a level of not more than 0.1 ppm water. With increasing feedstock water content the catalysts are found to deactivate. It also is quite desirable to dry the catalyst thoroughly immediately prior to use. This can be successfully done by heating my catalysts in a dry, unreactive gas such as air or nitrogen at a temperature of at least 150° C., but preferably at even higher temperatures. The time needed for adequate drying will depend on such factors as gas flow rate and temperature, but at 300° C. a time from 6 to about 12 hours appears adequate. The catalytic composites of my invention also are quite sensitive to other materials as well, such as organic nitrogen compounds, organic oxygenates, and sulfur compounds generally. Thus, it is preferable to use feedstocks containing less than 0.1 ppm nitrogen, less than 0.2 ppm oxygenates, and less than 10 ppm sulfur.

Alkylation of benzene by the detergent-range linear monoolefins of this invention may be conducted either as a batch method or in a continuous manner, although the latter is greatly preferred and therefore will be described in some detail. The composites of this invention used as catalyst may be used as a packed bed or a fluidized bed. Feedstock to the reaction zone may be passed either upflow or downflow, or even horizontally as in a radial bed reactor. The admixture of benzene and the feedstock containing the total linear monoolefins is introduced at a total benzene:olefin ratio of between 5:1 and 30:1, although usually the ratio is in the range between about 8:1 and 20:1. In one desirable variant olefin may be fed into several discrete points within the reaction zone, and at each zone the benzene:olefin ratio may be greater than 30:1. However, the total benzene:olefin ratio used in the foregoing variant of my invention still will be within the stated range. The total feed mixture, that is, benzene plus feedstock containing linear monoolefins, is passed through the packed bed at a liquid hourly space velocity (LHSV) between about 0.3 and about 6 $hr^{-1}$ depending upon alkylation temperature, how long the catalyst has been used, the ratio of silica to alumina and fluoride level in the catalyst, and so on. The temperature in the reaction zone will be maintained at between about 60 and about 140° C., and pressures generally will vary between about 200 and about 1000 psig (1379–6895 kPa) to ensure a liquid phase alkylation. After passage of the benzene and linear monoolefin feedstock through the reaction zone, the effluent is collected and separated into benzene, which is recycled to the feed end of the reaction zone, paraffin, which is recycled to the dehydrogenation unit, and alkylated benzenes. The alkylated benzenes are usually further separated into the monoalkyl benzenes, used in subsequent sulfonation to prepare the linear alkylbenzene sulfonates, and the oligomers plus polyalkylbenzenes. Since the reaction usually goes to at least 98% conversion, little unreacted monoolefin is recycled with paraffin.

For alkylation other than detergent alkylation, i.e., in the more general case, the reaction between the alkylatable aromatic compound and the alkylating agent will also be performed generally as described above. Whether the aromatic or the alkylating agent is used in excess depends upon the relative economics of the process, the desirability of the predominance of a particular product, the tendency toward oligomerization of, for example, the olefin, and so forth. However, in general the ratio of the alkylatable aromatic substrate and alkylating agent may range between about 1:20 and 20:1. As stated previously, alkylation temperatures will be in the range of 60–400° C., although temperatures between 100 and 225° C. are more the norm. Pressures will be adequate to ensure a liquid phase alkylation and usually will be no more than about 500 pounds per square inch, although in the case of lower olefins higher temperatures up to perhaps 2,000 psig may be employed. Whether there is recycling of any of the unreacted components will depend, inter alia, upon the extent of conversion, the economic value of the reactant, the ease with which the unreacted materials are separated from the reaction products, and so forth.

For either type of alkylation we have observed that the presence of chloride at low levels is necessary to initiate alkylation. Among the chlorides which may be used in the practice of this invention are included alkyl chlorides, which under reaction conditions undergo dehydrohalogenation with formation of HCl. Hydrogen chloride itself also may be used directly, instead of generating it from an alkyl chloride. It is common to use an alkyl chloride which may be of the same carbon number as the alkylation agent (i.e., olefin). Examples of alkyl chloride commonly used include butyl chloride, pentyl chloride, hexyl chloride, octyl chloride, nonyl chloride, decyl chloride, and so on. Since secondary alkyl chlorides dehydrohalogenate more readily than do primary alkyl chlorides they are somewhat favored over the latter. Of course, tertiary alkyl chlorides also may be used in the practice of this invention. Whatever halide is the source of HCl, it is present in an amount sufficient to afford from about 5 up to about 5000 ppm chloride, preferably from 50 to about 500 ppm chloride. Hydrogen chloride per se may be used directly at the foregoing concentrations.

The following examples are illustrative only. They show in some detail how the invention claimed below may be carried out but are not intended to limit the invention in any way.

EXAMPLE 1

General Procedure. Catalyst was packed in a bed 0.5 inch in diameter and 8 inches long equipped with a sliding thermocouple to survey bed temperature at various depths. The feedstock containing linear monoolefins resulted from dehydrogenation of n-paraffins and had the composition given below.

TABLE 1

| Feedstock Composition (weight percent) | | |
|---|---|---|
| Branched hydrocarbons | | 7.9 |
| Unbranched hydrocarbons | | 92.1 |
| | Alkenes | Alkanes |
| C9 | <0.1 | 0.1 |
| C10 | 0.9 | 7.9 |
| C11 | 4.1 | 31.8 |
| C12 | 3.6 | 24.8 |

TABLE 1-continued

| Feedstock Composition (weight percent) | | |
|---|---|---|
| Branched hydrocarbons | | 7.9 |
| Unbranched hydrocarbons | | 92.1 |
| | Alkenes | Alkanes |
| C13 | 2.6 | 15.7 |
| C14 | 0.1 | 0.4 |
| Total | 11.3 | 80.7 |

The feedstock containing the linear monoolefins and benzene at a molar ratio of 10:1 benzene:olefin was fed upflow to the packed bed of catalyst at conditions given in the table. Effluent was analyzed by gas chromatography. Analyses were performed after the reactor had lined out, that is, after equilibrium had been attained.

Alkylation with catalytic composites. $AlCl_3$ supported on 1 wt. % K modified gamma alumina was tested for the alkylation of benzene with normal decene. This test was conducted in the presence of a small amount of n-octylchloride (the 1-chloro isomer). At 60° C. and about 80% decene conversion, about 97% linear decylbenzene was produced. Selectivity to monoalkylbenzene was about 90% at this condition (feed benzene/olefin=10). Conversion was increased to 97% by raising the temperature to 120° C. where linearity was about 93% and selectivity increased to about 94%. Higher conversion at lower temperature should be achievable by using a secondary Cl isomer.

EXAMPLE 2

Trace Metal Analyses of Aluminas. Alumina samples used as catalyst supports were routinely analyzed for trace metals. Typical results for three representative aluminas indicated as samples A–C, are given below; the sample identified as "Kaiser" is a commercial alumina from Kaiser Alumina sold under the name Versal-250.

TABLE 4

| Trace Metals in Alumina | | | | |
|---|---|---|---|---|
| Metal (in ppm) | Sample A | Sample B | Sample C | Kaiser |
| Na | 98 | 20 | 23 | <1000 |
| Mg | <10 | 30 | <10 | <100 |
| Ca | <300 | <300 | <300 | <300 |
| Cu | <10 | <10 | | <10 |

Two types of commercial aluminas as well as an alumina routinely prepared for applicants were analyzed for trace metals by Galbraith Laboratories, an independent and well known analytical laboratory. Results obtained by them are found in Table 5. Catapal is a commercial alumina made by Vista. Versal-250 is a commercial alumina made by Kaiser Alumina; this sample is different from the one above. Sample D is an alumina routinely prepared by applicants' assignee.

TABLE 5

| | Trace Analyses by Independent Laboratory | | |
|---|---|---|---|
| Metal (in ppm) | Catapal | Versal-250 | Sample D |
| Na | 1400 | 1850 | 1720 |
| K | 380 | 380 | 400 |
| Ca | <35 | 85 | 114 |
| Mg | <35 | <34 | <26 |

The foregoing data show the maximum amounts (in ppm) of trace metals in various types of commercial alumina is:

Na<2000 ppm

K≦400 ppm

Ca<300 ppm

Mg<35 ppm

Cu<10 ppm

These maximum levels are representative of those found in aluminas from various sources and demonstrate that the amounts added by applicants are far in excess of what may be reasonably expected to occur in merchant alumina.

What is claimed is:

1. In the method for alkylating benzene with one or more linear monoolefins with at least 90% selectivity of olefin conversion to monoalkylbenzenes, and with at least 90% linearity with respect to monoalkylbenzene formation comprising reacting benzene with the linear monoolefins in a feedstock at alkylating conditions and in the presence of a catalyst, said feedstock containing at least one linear monoolefin, said alkylating conditions including reacting from about 5 to about 30 molar proportions of total benzene for each molar proportion of total linear monoolefins at a temperature from about 60° C. to about 140° C. and a pressure from about 200 to about 1000 psig, where the catalyst comprises a) a refractory inorganic oxide, b) the reaction product of a first metal halide and bound surface hydroxyl groups of said refractory inorganic oxide, c) a second metal cation, and d) optionally a zerovalent third metal; where said refractory inorganic oxide is selected from the group consisting of alumina, titania, zirconia, chromia, silica, boria, silica-alumina, and combinations thereof; said first metal halide is a fluoride, chloride, or bromide of aluminum; said second metal cation is selected from the group consisting of a) monovalent metal cations in an amount from 0.0026 up to about 0.20 gram atoms per 100 grams refractory inorganic oxide for lithium, potassium, cerium, rubidium, silver, and copper, and in an amount from 0.012 to about 0.12 gram atoms for sodium, and b) alkaline earth metal cations in an amount from about 0.0013 up to about 0.01 gram atoms per 100 grams of refractory inorganic oxide for beryllium, strontium, and barium, and an amount from about 0.004 up to about 0.1 gram atoms per 100 grams support for magnesium and calcium, and any combination thereof; and said third metal is selected from the group consisting of platinum, palladium, nickel, ruthenium, rhodium, osmium and iridium, and any combination thereof; the improvement comprising using a feedstock containing less than 0.1 ppm nitrogen, less than 0.2 ppm oxygenates, less than 0.1 ppm water, and less than 10 ppm sulfur.

2. The method of claim 1 where the molar ratio of benzene to linear monoolefins is from about 8 to about 20.

3. The method of claim 1 where the temperature does not exceed 135° C.

4. The method of claim 1 where the monoolefins have from about 6 to about 20 carbon atoms.

5. The method of claim 4 where the monolefins have from about 8 to about 16 carbon atoms.

6. The method of claim 5 where the monoolefins have from about 10 to about 14 carbon atoms.

7. The process of claim 1 where alkylating conditions include a temperature from about 60 up to about 400° C. and a cofeed of HCl or an alkyl chloride at concentrations effective to afford from 5 up to about 5000 ppm chloride.

8. The process of claim 1 where the refractory inorganic oxide is alumina.

9. The process of claim 8 where the alumina is a gamma, theta, or eta alumina.

10. The catalytic composite of claim 1 where the second metal cation is selected from the group consisting of lithium, sodium, potassium, cesium, rubidium, silver, copper(I), beryllium, magnesium, calcium, strontium and barium.

11. The process of claim 1 where the second metal cation is an alkali metal cation.

12. The catalytic composite of claim 1 where the second metal is potassium.

13. The process of claim 1 where the third metal is palladium, platinum, nickel, and combinations thereof.

* * * * *